United States Patent [19]

Eggensperger et al.

[11] Patent Number: 5,185,145
[45] Date of Patent: Feb. 9, 1993

[54] DISINFECTANT CONCENTRATE AND ITS USE AS A MYCOBACTERICIDE AND VIRICIDE

[75] Inventors: Heinz Eggensperger, Hamburg; Karl-Heinz Diehl, Norderstedt; Helmut Nolte, Tangstedt; Helmut Rackur, Bebensee; Ute Eggers-Maass, Hamburg; Michael Mohr, Kaltenkirchen; Lower Bernd; Wolfgang Beilfuss, both of Hamburg, all of Fed. Rep. of Germany

[73] Assignee: Eastman Kodak Company, Rochester, N.Y.

[21] Appl. No.: 658,921

[22] Filed: Feb. 21, 1991

[30] Foreign Application Priority Data

Feb. 23, 1990 [DE] Fed. Rep. of Germany ....... 4005784

[51] Int. Cl.$^5$ .................... A01N 39/00; A01N 47/44
[52] U.S. Cl. ................... 424/78.08; 514/634; 514/635; 514/718; 514/731
[58] Field of Search ............... 514/634, 635, 718, 731; 424/78.08

[56] References Cited

U.S. PATENT DOCUMENTS

| | | | |
|---|---|---|---|
| 2,666,010 | 1/1954 | Stayner | 514/731 |
| 2,689,814 | 9/1954 | Nicholls et al. | 424/332 |
| 5,030,659 | 7/1991 | Bansemir et al. | 514/731 |

FOREIGN PATENT DOCUMENTS

0231080A1  1/1987  European Pat. Off.

Primary Examiner—Thurman K. Page
Assistant Examiner—Peter F. Kulkosky
Attorney, Agent, or Firm—John R. Everett

[57] ABSTRACT

The invention relates to a disinfectant concentrate containing 10 to 60% by weight of phenoxyethanol or a phenoxypropanol mixture of 2-phenoxy-1-propanol and 1-phenoxy-2-propanol in a ratio by weight of from 1:4 to 1:20, 0.1 to 50% by weight of a cationic compound selected from the group of the guanidinium compounds, quaternary ammonium compounds or mixtures of these, 3 to 25% by weight of non-ionic surfactants and 0.1 to 10% by weight of an organic nitrogen-containing base having a $pK_B$ value of $\geq 4.75$.

12 Claims, No Drawings

| # DISINFECTANT CONCENTRATE AND ITS USE AS A MYCOBACTERICIDE AND VIRICIDE

FIELD OF THE INVENTION

The invention relates to a disinfectant concentrate.

BACKGROUND OF THE INVENTION

Disinfectant concentrates are described, for example, by O. G. Clausen and coworkers in "Medd. Nor. Farm. Selsk. 39 (1977) 187-204" and furthermore, in particular in connection with chlorohexidine as a representative of the guanidinium compounds, in EP 0,231,080-A1. These disinfectants indeed have the advantage that they are free of aldehydes and phenols, but they lack effectiveness against mycobacteria, such as Mycobacterium tuberculosis; moreover, these preparations are ineffective against many uncoated viruses, such as, for example, polio viruses, even when used in high concentrations.

Moreover, the disinfectants of the prior art, which are in the neutral range of about pH 5 to 8, or disinfectants as claimed in EU 0,231,080-A1 are adjusted to higher pH values with mineral bases such as, for example, sodium hydroxide solution, they usually do not give ph-stable formulations; the pH drops considerably within a few weeks; the disinfectants lose their effectiveness against mycobacteria and also as viricides after only a short storage time.

It was an object of the invention to propose a disinfectant concentrate which, on the one hand, is economical and, on the other hand, has a prolonged shelf-Life and is therefore stable, and which can be used in particular as a mycobactericide and viricide when diluted appropriately.

SUMMARY OF THE INVENTION

To achieve this object, there is provided an aqueous disinfectant concentrate with a content of phenoxyalcohol, a cationic compound and non-ionic surfactants, which contains
 a) 10 to 60% by weight of phenoxyethanol or a phenoxy-propanol mixture of 2-phenoxy-1-propanol and 1-phenoxy-2-propanol, in a ratio by weight of from 1:4 to 1:20;
 b) 0.1 to 50% by weight of a cationic compound, selected from the group of the guanidinium compounds, quaternary ammonium compounds or their mixtures;
 c) 3 to 25% by weight of non-ionic surfactants and
 d) 0.1 to 10% by weight of an organic nitrogen-containing base with a $pK_B$ value $\geq 4.75$ for establishing a pH of from 7.8 to 11 in the disinfectant concentrate.

Surprisingly, it has emerged that certain phenoxyalkanols, i.e., a very particular phenoxypropanol mixture and/or phenoxyethanol in combination with the cationic surfactants selected to suit the intended purpose, cause an increase in activity by selected alkalization.

More particularly when an organic nitrogen compound having $Pk_B$ value is higher than 4.75 is used as an alkalization component, it is possible to prepare a pH-stable formulation which shows a surprising effectiveness against Mycobacterium tuberculosis. This effectiveness also extends to Mycobacterium terrae, which is typical as a test bacterium for this range. Moreover, an effectiveness against polio viruses has been noticed.

DETAILS OF THE INVENTION

The phenoxyalcohol in the disinfectant concentrate is employed in an amount of from 10 to 60% by weight and, in the case of a phenoxypropanol, preferably in an amount of from 35 to 45% by weight and in particular in an amount of about 40% by weight. If phenoxyethanol is used, it is preferably present in an amount of from about 10 to 20% by weight. For economic reasons, it is preferred to use the phenoxypropanol mixture mainly in a ratio by weight of 2-phenoxy-1-propanol to 1-phenoxy-2-propanol in a range of from 1:4 to 1:20, preferably in a range of from 1:4 to 1:10, and in particular at 1:6.

The cationic compound is selected from the group of the quaternary ammonium compounds, guanidinium compounds or their mixtures. Preferred quaternary ammonium compounds are benzalkonium chloride, cetylpyridinium chloride, didecyldimethylammonium chloride or related compounds. If low foaming is particularly desired, it is also possible to use polymeric quaternary ammonium compounds.

The preferred guanidinium compound is coconut propylenediamineguanidinium diacetate, but it is also possible to use other guanidinium compounds, such as oligohexamethylene biguanide.

The benzalkonium chloride preferably contains equal amounts of $C_{12}$- and $C_{14}$-alkyl radicals.

The polymeric quaternary ammonium compound which is preferably employed is polyhydroxyethylene-(dimethylamino)-hydroxypropyl-(dimethylamino)-methylene dichloride.

The cationic compound is employed in amounts of from 0.1 to 50% by weight, preferably in amounts of from 5 to 30, and in particular in amounts of 16.5, % by weight.

The third component present are 3 to 25% by weight of known non-ionic surfactants, such as, for example, reaction products from alkylene oxide and longer-chain alkanols of various origins, alkoxylated fatty alcohols, in particular those having 10 to 18 carbon atoms and 7 to 14 ethoxy or propoxy units being preferred.

An essential component is the alkalizing agent, which can generally be present in amounts of from 0.1 to 10% by weight and which is an organic nitrogen-containing base with a $pK_B$ value equal to, or greater than, 4.75. In the above-mentioned range of amounts there is used such an amount of this organic nitrogen base that a pH of from 7.8 to 11 and preferably from 8.2 to 9.8 is established in the disinfectant concentrate, since, at this alkalinity, the synergistic compensation for the existing lack of effectiveness against mycobacteria and viruses is achieved particularly well.

Alkalizing agents of this type which have a synergistic increase in view of the mycobactericides and viricides are generally amines or aminopolyols and basic amino compounds, with aminopolyols and, in particular, tetrakis-(2-hydroxypropyl)-N,N,N',N'-ethylenediamine, being particularly preferred.

The mechanism of action of the specific alkalizing agents which act as synergists in view of the lack of effectiveness of the mycobactericides and viricides has not yet been elucidated; however, it is assumed that the organic nitrogen-containing alkalizing agents with a $Pk_B$ value of more than 4.75 are less affected by the other constituents of the disinfectant concentrate than customary alkalizing agents such as, for example, mineral bases.

The disinfectant concentrates furthermore contain the customary remaining components such as water and other customary additives such as solubilizers, corrosion inhibitors, perfume and colorants.

The concentrates are stable products with a constant pH in a range of from 7.8 to 11 and preferably from 8.2 to 9.8, which is essential for the long-term action as mycobactericide and viricide.

These concentrates are preferably employed in a concentration of from. 0.2 to 10% by weight, namely in particular for the disinfection of surfaces such as floors and objects in the domestic sector and in the sanitary sector. In particular, they are used in the medical sector for the disinfection of instruments and apparatuses and for disinfection or decontamination after industrial accidents; their use in scrubbers of climatic chambers is also possible, the weakly alkaline pH being advantageous with a view to the prevention of corrosion.

In what follows, the invention will be illustrated in greater detail with the aid of examples.

EXAMPLE 1

A disinfectant concentrate of the following composition was prepared.

| | |
|---|---|
| Mixture of 2-phenoxy-1-propanol and 1-phenoxy-2-propanol in a ratio by weight of 1:6 | 40% by weight |
| Coconut propylenediamineguanidine diacetate | 7% by weight |
| Condensation product of a $C_{10}$ alcohol with 11 ethylene oxide units | 5% by weight |
| Tetrakis-(2-hydroxypropyl)-N,N,N',N'-athylenediamine | 5% by weight |
| Water, corrosion inhibitors, colorants and perfume | to 100 |

Microbial substrate tests with Mycobacterium terrae without and with exposure to albumin load as per the "Richtlinien Ear die Priifunc chemischer Desinfektionsmittel (Guidelines for Testing Chemical Disinfectants)" chapter 36 of the Deutsche Gesellschaft fur Hygiene und Mikrobiologie (German Hygenic and Microbiological Society) gave the data listed in Table 1 below:

TABLE I

| Disinfectant Concentration | Time in Minutes | | | | |
|---|---|---|---|---|---|
| | 15' | 30' | 45' | 60' | 120' |
| A (without exposure) | | | | | |
| 2% | + | + | − | − | − |
| 3% | − | − | − | − | − |
| 4% | − | − | − | − | − |
| B (with exposure) | | | | | |
| 2% | + | + | − | − | − |
| 3% | + | − | − | − | − |
| 4% | + | − | − | − | − |

EXAMPLE 2

A disinfectant concentrate was prepared with the following constituents:

| | |
|---|---|
| Phenoxypropanol mixture with a ratio by weight of 2-phenoxy-1-propanol to 1-phenoxy-2-propanol of 1:6 | 40% by weight |
| Benzalkonium chloride | 20% by weight |
| Coconut propylenediamineguanidine diacetate | 7% by weight |
| Condensation product of a $C_{10}$-alcohol with 11 ethylene oxide units | 5% by weight |
| Tetrakis-(2-hydroxypropyl)-N,N,N',N'-ethylenediamine | 5% by weight |
| Water and other additives | to 100 |

COMPARISON TEST 2A

As a comparison, a formulation was prepared in accordance with Example 2, but without the alkalizing agent tetrakis-(2-hydroxypropyl)-N,N,N',N'-ethylenediamine. The microbial substrate tests with Mycobacterium terrae are listed in Table II below:

TABLE II

| Disinfectant Concentration | Time in Minutes | | | | |
|---|---|---|---|---|---|
| | 15' | 30' | 45' | 60' | 120' |
| Concentrate in accordance with Example 2 | | | | | |
| A (without exposure) | | | | | |
| 3% | + | + | − | − | − |
| 4% | + | − | − | − | − |
| 5% | − | − | − | − | − |
| B (with exposure) | | | | | |
| 3% | + | + | + | − | − |
| 4% | − | − | − | − | − |
| 5% | − | − | − | − | − |
| Comparison test (without alkalizing agent) | | | | | |
| A (without exposure) | | | | | |
| 3% | + | + | + | + | + |
| 4% | + | + | + | + | − |
| 5% | + | + | + | + | − |
| B (with exposure) | | | | | |
| 3% | + | + | + | + | + |
| 4% | + | + | + | + | + |
| 5% | + | + | + | − | − |

It can be seen from the above table that the disinfectant concentrate in accordance with Example 2 containing 5% of tetrakis-(2-hydroxypropyl)-N,N,N',N'-ethylenediamine shows considerably better values.

EXAMPLE 3

A disinfectant concentrate of the following composition was prepared;

| | |
|---|---|
| Phenoxypropanol mixture of 1-phenoxy-2-propanol and 2-phenoxy-1-propanol in a ratio by weight of 1:6 | 40% by weight |
| Benzalkonium chloride ($C_{12}:C_{14}$ = 1:1) | 20% by weight |
| Tetrakis-(2-hydroxypropyl)-N,N,N',N'-ethylenediamine | 5% by weight |
| Oxethylated $C_{10}$-alcohol with 11 EO units | 5% by weight |
| Water, corrosion inhibitors, colorants and perfume | to 100 |

Without exposure, a 3%, 4% and 5% dilution of this concentrate was compared with a comparison product which did not contain an alkalizing component. The results are listed in Table III below.

TABLE III

| | Time in Minutes | | | | |
|---|---|---|---|---|---|
| | 15' | 30' | 45' | 60' | 120' |
| Concentrate in accordance with Example 3 | | | | | |
| Disinfectant Concentration | | | | | |
| 3% | + | + | − | − | − |
| 4% | + | − | − | − | − |
| 5% | − | − | − | − | − |
| Comparison Test | | | | | |
| 3% | + | + | + | + | + |

TABLE III-continued

| Concentrate in accordance with Example 3 | | | | | |
|---|---|---|---|---|---|
| | Time in Minutes | | | | |
| | 15' | 30' | 45' | 60' | 120' |
| 4% | + | + | + | + | − |
| 5% | + | + | + | + | − |

From the above values there is clear evidence for the superiority of the concentrate according to the invention in accordance with Example 3.

EXAMPLE 4

A disinfectant concentrate of the following composition was prepared:

| | |
|---|---|
| Phenoxyethanol | 17.5% by weight |
| Benzalkonium chloride | 9.5% by weight |
| Condensation product of a $C_{10}$-alcohol with 11 ethylene oxide units | 2.5% by weight |
| Condensation product of a $C_{12}$-alcohol with 3 ethylene oxide units | 2.5% by weight |
| Tetrakis-(2-hydroxypropyl)-N,N,N',N'-ethylenediamine | 5.0% by weight |
| Water, corrosion inhibitor, colorant and perfume | to 100 |

To compare the pH-stability of the disinfectant concentrate, a formulation was prepared in accordance with Example 4 but a pH of 9.5 was established using sodium hydroxide solution in place of 5% of the alkalizing agent tetrakis(2-hydroxypropyl)-N,N,N',N'-ethylene-diamine.

| | | Immediately | 3 Months |
|---|---|---|---|
| pH | Example 4: | 9.5 | 9.5 |
| | Comparison: | 9.5 | 7.5 |

This comparison shows the supreme stability of the formulation adjusted according to the invention with the alkalizing agent.

The invention has been described in detail with particular reference to preferred embodiments thereof, but it will be understood that variations and modifications can be effected within the spirit and scope of the invention.

We claim:

1. An aqueous disinfectant concentrate having a pH of from 7.8 to 11 with a content of phenoxyalcohol, a cationic compound and non-ionic surfactants, which contains a) 10 to 60% by weight of phenoxyethanol or a phenoxy-propanol mixture of 2-phenoxy-1-propanol and 1-phenoxy-2-propanol, in a ratio by weight of from 1:4 to 1:20,
   b) 0.1 to 50% by weight of a cationic compound, selected from the group of the guanidinium compounds, quaternary ammonium compounds or their mixtures,
   c) 3 to 25% by weight of non-ionic surfactants and
   d) 0.1 to 10% by weight of tetrakis-(2-hydroxypropyl)-N,N,N', N'-ethylenediamine.

2. A disinfectant concentrate as claimed in claim 1, which contains 35 to 45% by weight of the phenoxy-propanol mixture.

3. A disinfectant concentrate as claimed in claims 2 or 1, wherein the ratio by weight of the 1-ol compound to the 2-ol compound is from 1:4 to 1:20 in the phenoxy-propanol mixture.

4. A concentrate as claimed in one of claims 2 or 1, wherein the ratio by weight of 2-phenoxy-1-propanol to 1-phenoxy-2-propanol is in a range of 1:6.

5. A disinfectant concentrate as claimed in claim 1, which contains from 10 to 20% by weight of phenoxyethanol.

6. A disinfectant concentrate as claimed in any one of claims 2 or 1, which contains from 5 to 30% by weight of the cationic compound.

7. A disinfectant concentrate as claimed in claim 6, which comprises, as a cationic compound, coconut propylenediamineguanidine diacetate, oligohexamethylene biguanide or mixtures of these.

8. A disinfectant concentrate as claimed in claim 6, which contains, as the cationic compound, a benzalkonium chloride with approximately equal amounts of $C_{12}$- and $C_{14}$-alkyl radicals.

9. A disinfectant concentrate as claimed in claim 6, which contains, as cationic compound, polyhydroxyethylene-(dimethylamino)-hydroxypropyl-(dimethylamino)-methylene dichloride.

10. A disinfectant concentrate as claimed in claim 6, which contains, as non-ionic surfactant, an alkoxylated fatty alcohol having 10 to 18 carbon atoms and 7 to 14 ethoxy or propoxy units.

11. A disinfectant concentrate as claimed in claim 6, which has a pH of from 8.2 to 9.8.

12. A method of disinfecting comprising applying to a surface a concentrate as claimed in claims 2 or 1 in a concentration of from 0.2 to 10% by weight based on the aggregate weight of the active substance components consisting of phenoxyalcohol, the cationic compound and the non-ionic surfactant, as a mycobactericide and viricide.

* * * * *